United States Patent [19]

Matsumoto et al.

[11] 4,425,436

[45] Jan. 10, 1984

[54] PROCESS FOR THE PRODUCTION OF AMINE OXIDASE

[75] Inventors: Kunio Matsumoto, Mishima; Masaki Takada, Shizuoka, both of Japan

[73] Assignee: Toyo Jozo Kabushiki Kaisha, Shizuoka, Japan

[21] Appl. No.: 351,486

[22] Filed: Feb. 23, 1982

[30] Foreign Application Priority Data

Feb. 23, 1981 [JP] Japan ................................ 56-24231

[51] Int. Cl.$^3$ .......................... C12P 7/00; C12N 9/02; C12N 9/88; C12N 1/14
[52] U.S. Cl. .................................. 435/191; 435/147; 435/232; 435/254; 435/814; 435/911
[58] Field of Search ............... 435/254, 147, 191, 232, 435/814, 911

[56] References Cited

U.S. PATENT DOCUMENTS 4,371,621  2/1983  Yamada et al. ..................... 435/191

FOREIGN PATENT DOCUMENTS 3048875 10/1981 Fed. Rep. of Germany ...... 435/191
57-50887  3/1982 Japan ................................ 435/191

*Primary Examiner*—Thomas G. Wiseman
*Assistant Examiner*—Deborah A. Grossman
*Attorney, Agent, or Firm*—Young & Thompson

[57] ABSTRACT

A process for the production of amine oxidase, which comprises culturing an amine-oxidase-producing microorganism belonging to the genus Talaromyces, genus Eupenicillium, genus Petromyces, genus Neosartorya or genus Eurotium, and isolating the thus-prepared amine oxidase from the cultured medium. The preferred strains of microorganisms under these genera are *Talaromyces flavus* var. *flavus* M 4175 FERM-P No. 5866, *Eupenicillium parvum* M 5051 FERM-P No. 5870, *Petromyces alliaceus* M 4648 FERM-P No. 5867, *Neosaytorya fischeri* M 4690 FERM-P No. 5868 and *Eurotium chevalieri* M 4805 FERM-P No. 5869.

1 Claim, 15 Drawing Figures

PROCESS FOR THE PRODUCTION OF AMINE OXIDASE

This invention relates to a process for the production of amine oxidase.

Amine oxidase is an enzyme which catalyzes the oxidative deamination of amines such as monoamines and diamines, and catalyzes the reaction which form one mole of aldehyde, hydrogen peroxide and ammonia from one mole of amine, oxygen and water, as follows:

$$RCH_2NH_2 + O_2 + H_2O \longrightarrow RCHO + NH_3 + H_2O_2$$

monoamine      aldehyde

Amine oxidase is widely distributed in animals, plants and microorganisms and has been known to be the enzyme which metabolizes amines. Many kinds of amine oxidases have been purified and their enzymatic nature is well known at present. The origin of these known amine oxidases can be animal serum such as porcine serum and bovine serum, animal tissues such as bovine liver, bovine brain and procine kidney, fungi such as genus Aspergillus, genus Penicillium, genus Monascus, genus Rhizopus, genus Mucor and genus Fusarium (see Japanese Patent Publ. No. 44-10959), bacteria such as *Sarcina lutea, Micrococcus vufens, Serratia marcescens*, and plant tissues such as Leguminosae.

We have found that amine oxidase is produced by culturing microorganisms which have not been previously known to produce amine oxidase, such as *Talaromyces flavus* var. *flavus* M 4175 belonging to the genus Talaromyces, *Eupenicillium parvum* M 5051 belonging to the genus Eupenicillium, *Petromyces alliaceus* M 4648 belonging to the genus Petromyces, *Neosartorya fischeri* M 4690 belonging to the genus Neosartorya and *Eurotium chevalieri* M 4805 belonging to the genus Eurotium.

The taxonomical properties of the microorganism strains recited hereinabove are as follows:

I. *Talaromyces flavus* var. *flavus* M 4145

The strain was isolated from a soil sample collected from a rice field at Nirayama-cho, Shizuoka-ken, Japan.

1. Growth conditions on various media (a) Malt extract agar:

Normal growth. 32–35 mm at 26° C. upon one week culture. Microbial flora: slightly thick, smooth surface and slightly cottony. Bright (hue 1 na)—bright yellow (hue 2 la). Many ascocarps of light lemon yellow (hue 1 ga). Smooth edges. No formation of soluble pigment and exudate. Color of reverse side: light yellow (hue 1½ ea).

(b) Czapek agar:

Normal growth. 20–22 mm at 26° C. for one week culture. Pale yellow (hue 1 ca) and fimbriae-like aerial hyphae appearing at an early stage. Light lemon yellow (hue 1 ga)—melon yellow (hue 3 ga) upon maturation of the ascocarps. Smooth edges. No formation of soluble pigment and exudate. Color of reverse side: wine (hue 7 pg).

(c) Oatmeal agar:

Normal growth. 35–37 mm at 26° C. upon one week culture. Microbial flora: slightly thin and cottony. Light lemon yellow (hue 1 ga). Ascocarps: well matured, and less in number than on malt extract agar. Smooth edges. No formation of soluble pigment or exudate. Color of reverse side: canary yellow (hue 1 ea).

2. Microscopic observation

Ascocarps: spherical-ovoid. Octaspores, diameter 8–10 μm. Ascospores: oval, 4.5–5.5×2.5–3 μm spiny spike. Conidia stage: Penicillium. Penicilli: biverticillata-symmetrica. Conidiophore: 100–300×3–3.5 μm, smooth wall. Metulae: 8–10×2.5–3 μm, smooth surface. Conidia: oval, 2.5–3.5×2–2.5 μm, smooth surface.

3. Physiological properties:

Growth pH: 2–8
Optimum pH: 3–7
Growth temperature: 13°–42° C.
Optimum temperature: 28°–33° C.

Considering the above taxonomical properties, the strain M 4175 is referred to as Ascomycetes having imperfect stage Penicillium. Genera Eupenicillium, Hamigera and Talaromyces are known genera having imperfect stage Penicillium. The strain in question is referred to as belonging to the genus Talaromyces because of having hyphae of reticulate ascocarps wall and linked asci. Furthermore, the properties of having yellow-colored ascocarps, oval ascospores with no apophyses and valleculae, and wholly spiny spikes below 5.5 μm, are identical with *Talaromyces flavus* var. *flavus*. The strain is referred to as *Talaromyces flavus* var. *flavus* M 4175. The strain is deposited in the Fermentation Institute, Japan as deposit No. FERM-P No. 5866.

II. *Eupenicillium parvum* M 5051

This strain was isolated from a soil sample collected from a ginger field at Minamikushiyama-mura, Nagasaki-ken, Japan.

1. Growth on various media (a) Malt extract agar:

Slow growth. 13–17 mm at 26° C. for one week culture. Microbial flora: gradually thicker toward the center, smooth surface. Chestnut brown (hue 4 ni). Slight formation of soluble pigment. Light wheat (hue 2 ca). No exudate. Smooth edges. Reverse: light tan (hue 3 gc).

(b) Czapeck agar:

Slow growth. 8–9 mm at 26° C. upon one week culture. Microbial flora: thickly swelled, smooth surface, bamboo (hue 2 gc). Edges: arachnoid. No formation of soluble pigment or exudate. Reverse: baby pink (hue 7 ca).

(c) Oatmeal agar:

Slow growth. 12–13 mm at 26° C. upon one week culture. Microbial flora: thin and flat, honey gold (hue 2 ic). Good formation of ascocarps. Edges: smooth. No formation of soluble pigment. Formation of exudate. Colorless. Reverse: light wheat (hue 2 ca).

2. Microscopic observation

Ascocarps: hard and sclerotia-like shapes, membranous wall. Spherical-semispherical. 7–9 μm in diameter. Ascospores are lens-shaped and have two separated ridges. 2–2.5×1.5–2 μm. Conidia stage: Penicillium. Penicilli: monoverticillata. Conidiophores: 20–50×1-.5–2 μm, smooth surface. Sterigma: 7–8×1.5–2 μm, smooth surface. Conidiospore: semispherical-oval, 1.5–2×1–1.5 μm, smooth surface.

3. Physiological properties

Growth pH: 2–9
Optimum pH: 3–7
Growth temperature: 20°–40° C.
Optimum temperature: 28°–32° C.

According to the above taxonomical properties, the strain M 5051 is Ascomycetes having imperfect stage Penicillium. Eupenicillium, Talaromyces and Hamigera are known genera having imperfect stage Penicillium. This strain is confirmed to belong to the genus Eupenicillium due to having hard sclerotia and membranous wall. The strain is identified as *Eupenicillium parvum* by the properties such as small ascospores of 2–2.5×1.5–2 μm, lens-shaped, two separated ridges and spiny spike surface. This strain is referred to as *Eupenicillium parvum* M 5051, and was deposited in the Fermentation Institute, Japan as permanent culture collection FERM-P No. 5870.

III. *Petromyces alliaceus* M 4648

This strain was isolated from a soil sample collected from a mountain at Ogasawara-mura, Tokyo, Japan.

1. Growth conditions on various media (a) Malt extract agar:
Rapid growth. 56–59 mm at 26° C. upon one week culture. Cottony surface, white or light ivory (hue 2 ca) at early stage of culture, and honey gold (hue 2 ic) depending upon the formation of conidiospores. Smooth edges. Black sclerotia are formed upon 20 days culture. No formation of soluble pigment or exudate. Reverse: light wheat (hue 2 ea).

(b) Czapek agar:
Slightly rapid growth. 44–48 mm at 26° C. upon one week culture. White cottony. Light ivory (hue 2 ca) upon more than 10 days culture. No formation of sclerotia. Smooth edges. No formation of soluble pigment or exudate. Reverse: light wheat (hue 2 ea).

(c) Oatmeal agar:
Rapid growth. 54 mm at 26° C. upon one week culture. Microbial flora: cottony but thick as compared with that on malt extract agar and Czapek agar. White to cream (hut 1½ ca) at an early stage of culture. Honey gold (hue 2 ic) depending upon the formation of conidiospores. Black sclerotia upon 15 days culture. Smooth edges. No formation of soluble pigment or exudate. Reverse: light yellow (hue 1½ ea).

2. Microscopic observation

Sclerotia: scattered forms on the surface of the medium. Black, oval-elliptical. 1–3 mm. Several spherical ascocarps in the sclerotia. Slow growth, 3 months or more. Asci: octaspores, spherical-semispherical, 15–17 μm, ascospores elliptical, 5–9×4.5–7 μm, colorless, smooth surface wall. Conidia stage: Aspergillus. Conidial head: 100–1000×6–8 μm, slightly yellowish, smooth wall. Vesicles: spherical-semispherical, 12–25 μm in diameter. Sterigma: bilayered, primary sterigma is 6–8×3.5–4.5 μm, secondary sterigma is 5–8×2–2.5 μm. Conidia: spherical-subspherical, 2.5–4 μm, slightly yellow.

3. Physiological properties

Growth pH: 1–11
Optimum pH: 3–9
Growth temperature: 13°–42° C.
Optimum temperature: 25°–32° C.

Nine genera have been known as microorganisms having imperfect stages of Aspergillus. Considering the above taxonomical properties, the strain No. 4648, having several ascocarps in the black sclerotia, belongs to the genus Petromyces. This strain is referred to as *Petromyces alliaceus* due to having large sclerotia of 1–3 mm and spherical-semispherical conidia. The strain is referred to as *Petromyces alliaceus* FERM-P No. 4648, and was deposited in the Fermentation Institute, Japan, as permanent culture collection No. FERM-P No. 5867.

IV. *Neosartorya fischeri* M 4690

This strain was isolated from a soil sample collected in a taro field at Ohito-cho, Tagatu-gun, Shizuoka-ken, Japan.

1. Growth on various media (a) Malt extract agar:
Rapid growth. 63–70 mm at 26° C., covering the whole area of Petri dish (inner diameter: 85 mm) at 37° C. upon one week culture. Microbial flora: thin and flat. White to slightly mist green (hue 23 ec) upon the formation of conidia. Smooth edges. No formation of soluble pigment or exudate. Ascocarps: abundant. Reverse: light wheat (hue 1½ ea).

(b) Czapek agar:
Rapid growth. 59 mm at 26° C., covering the whole area of a Petri dish (inner diameter 85 mm) at 37° C. upon one week culture. Other characteristics are the same as in the case of malt extract agar medium.

(c) Oatmeal agar:
Rapid growth. 50–60 mm at 26° C., covering the whole area of a Petri dish (inner diameter 85 mm) at 37° C. upon one week culture. Other characteristics are the same as in the case of malt extract agar medium.

2. Microscopic observation

Ascocarps: spherical, 200–300 μm, white. Asci: octaspores, oval-elliptical, 10–12×8–10 μm. Ascospores: lens-shaped, two ridges on an equator, 6–7×4–4.5 μm, colorless, spiny spikes on the wall. Conidia stage: Aspergillus. Conidial heads: cylindrical. Conidiophores: 100–400 μm, colorless, smooth wall. Vesicles: small, 12–14 μm in diameter, flask-shaped. Conidia: semispherical-elliptical, 2.5–3×2–2.5 μm, smooth to slightly rough wall.

3. Physiological properties

Growth pH: 2–10
Optimum pH: 4–7
Growth temperature: 13°–55° C.
Optimum temperature: 30°–35° C.

Considering the above taxonomical properties, having white ascocarps, thin cell wall, no Hülle cells and not abundant, the strain M 4649 is identical with the genus Neosartorya. Furthermore, the properties having linked humpy processus of ascospores are the properties of *Neosartorya fischeri* and so the strain M 4690 is referred to as *Neosartorya fischeri* M 4690 FERM-P No. 5868.

V. *Eurotium chevalieri* M 4805

This strain was isolated from a soil sample collected from a field in Fukue-shi, Nagasaki-ken, Japan.

1. Characteristics of various media (a) Malt extract agar:

Slow growth. 10–11 mm at 26° C. upon one week culture. Microbial flora: slightly thick and swelled, mustard tan (hue 2 lg). Edges: slightly arachnoid. Soluble pigment: honey gold (hue 2 ic). No exudate. Reverse: dark luggage tan (hue 4 pg).

(b) Czapek agar:

Slow growth. 10–13 mm at 26° C. upon one week culture. Microbial flora: slightly thin and flat. Golden brown (hue 3 pg). Edges: almost smooth. Soluble pigment: light wheat (hue 1½ ea). No exudate. Reverse: honey gold (hue 2 ic).

(c) 20% sucrose added Czapek agar:

Rapid growth. 45–50 mm at 26° C. upon one week culture (it can be said to resemble abundant fungi). Microbial flora: comparatively thin and flat. Ascocarps: good, bright yellow (hue 1½ la). Conidia abundant parts: antique gold (hue 1½ ne). Edges: slightly arachnoid. No soluble pigment or exudate formation. Reverse: mpale (hue 4 le) in center; bright yellow (hue 1½ la) at edges.

2. Microscopic observation

Ascocarps: spherical, 100–160 μm, yellowish olive color. Wall: membranous. Asci: spherical-semispherical, octaspores, 10–12 μm. Ascospores: lens-shape, 4–5×3.5–4 μm, two separated ridges, smooth wall. Conidia stage: Aspergillus. Conidial heads: branched, several radii. Conidiophores: 150–400×5–7 μm. Vesicles: flask shaped, 10–15 μm in diameter. Sterigma: single layer, 5–7×2–2.5 μm. Conidia: elliptical, rough, 5–7×4–5 μm.

3. Physiological properties

Growth pH: 2–10
Optimum pH: 4–7
Growth temperature: 20°–40° C.
Optimum temperature: 28°–33° C.

Considering the above taxonomical properties, having yellow colored ascocarps with thin wall cells, no Hülle cells, abundant growth, and good growth and maturation on substrates containing much sugar or sodium chloride, this strain is seen to belong to the genus Eurotium. Furthermore, the strain having properties of ascospores smaller than 6 μm, clearly divided two ridges and smooth walls, is referred to as *Eurotium chevalieri*, and is designated as *Eurotium chevalieri* M 4805. The strain is deposited in the Fermentation Institute, Japan and has its permanent culture collection number FERM-P No. 5869.

The identification of colors is based on the "Color Harmony Manual", 4th Ed., 1958, published by Container Corp. of America.

The present invention has been made possible by the discovery of the above microorganism strains and is a process for the production of amine oxidase which comprises culturing an amine-oxidase-producing microorganism strain belonging to the genus Talaromyces, genus Eupenicillium, genus Petromyces, genus Neosartorya or genus Eurotium, and isolating the thus-produced amine oxidase from the cultured medium.

The strains *Talaromyces flavus* var. *flavus* M 4175 FERM-P No. 5866, *Eupenicillium parvum* M 5051 FERM-P No. 5870, *Petromyces alliaceus* M 4648 FERM-P No. 5867, *Neosartorya fischeri* M 4690 FERM-P No. 5868 and *Eurotium chevalieri* M 4805 FERM-P No. 5869 used in the present invention are for the purpose of illustration and the amine-oxidase-producing artificial or natural mutants of the strains belonging to the genus Talaromyces, genus Eupenicillium, genus Petromyces, genus Neosartorya or genus Eurotium can also be used in the present invention.

In the present invention, the above amine-oxidase-producing microorganisms are cultured by a conventional process for the production of enzymes. Liquid culture is preferable; and for industrial production, submerged aeration culture is advantageous.

Conventional nutrient sources are used as media for what is otherwise a conventional microorganism culture. Assimilable carbon sources such as glucose, sucrose, lactose, maltose, fructose and molasses can be used, and assimilable nitrogen sources such as peptone, meat extract, yeast extract, casein hydrolyzate and potato extract can be used. Phosphates and other salts of magnesium, calcium, potassium, iron, manganese and zinc can also be used if desired.

Culturing temperatures can be varied depending upon the desired rate of growth of the microorganisms and amine oxidase production, and is preferably 25°–37° C. Culturing time can be varied depending on the culture conditions, and can be terminated upon achieving maximum production of amine oxidase, usually for 10–25 hours.

Amine oxidase is isolated from the thus-cultured media, and the enzyme of the present invention is an endo-enzyme.

The enzyme amine oxidase can be isolated by the following procedures:

The cultured microorganisms are separated by filtration or centrifugation, and the isolated cultured cells are ruptured by mechanical or enzymatic means such as lysozyme to solubilize the amine oxidase. A soluble salt such as ammonium sulfate or sodium chloride is added to the amine oxidase solution after concentration or without concentration, for salting out the enzyme. Or the enzyme solution can be treated by adding a water-miscible organic solvent such as methanol, ethanol or acetone to precipitate the enzyme. The precipitate dissolved in water is dialyzed with a semipermeable membrane to isolate the low molecular weight impurities. Impurities can also be removed by adsorption chromatography or ion-exchange chromatography using adsorption agents or gel filtration agents. The enzyme solution is concentrated in vacuo or lyophilized to obtain the partially purified enzyme powder. Further purification can be achieved by conventional purification methods for enzymes such as adsorption chromatography, ion-exchange chromatography or gel filtration.

In the accompanying drawings

The amine oxidase of the present invention is further characterized as follows, in which each enzyme is abbreviated as M 4805 for the enzyme produced by the cultivation of *Eurotium chevalieri* M 4805, M 4690 for the enzyme produced by the cultivation of *Neosartorya fischeri* M 4690, M 4648 for the enzyme produced by the cultivation of *Petromyces alliacius* M 4648, M 5051 for the enzyme produced by the cultivation of *Eupenicillium parvum* M 5051, and M 4175 for the enzyme produced by the cultivation of *Talaromyces flavus* var. *flavus* M 4175:

(1) Action

The enzyme catalyzes the reaction which forms an aldehyde, ammonia and hydrogen peroxide from a monoamine, oxygen and water:

$$RCH_2NH_2 + O_2 + H_2O \longrightarrow RCHO + NH_3 + H_2O_2$$

monoamine     aldehyde

(2) Optimum pH

An n-butylamine is used as substrate. An oxygen electrode is used for measurement. The following buffer solutions are used:
phosphate buffer: pH 6–8
Tris-HCl buffer: pH 9–10

Figure 1:
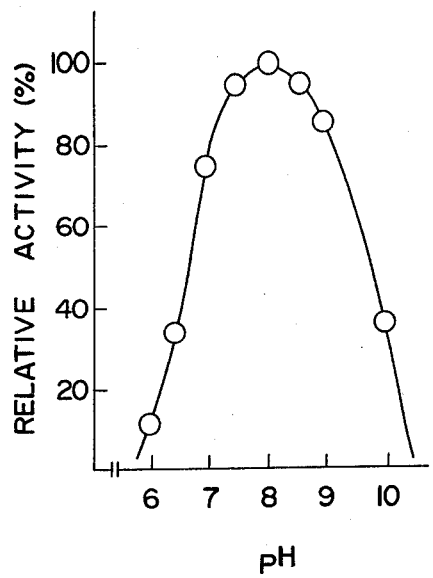
FIGS. 1–5 are optimum pH curves for amine oxidase prepared according to the present invention from each of the five preferred strains of microorganisms recited above.
Figure 2:
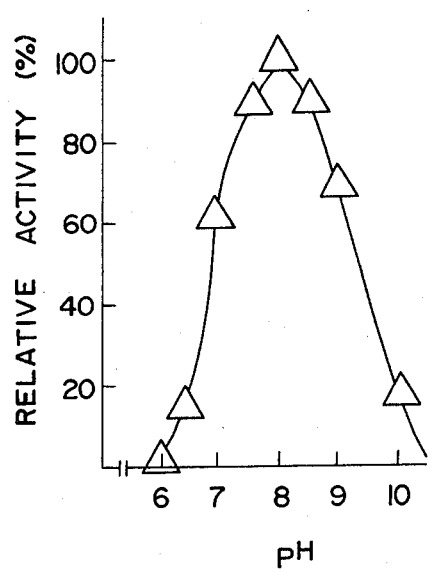
Figure 3:
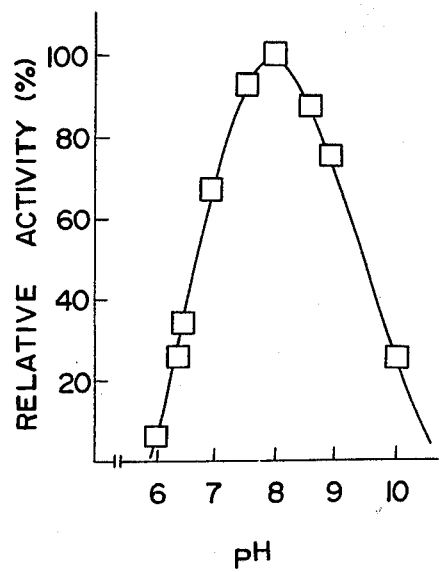
Figure 4:
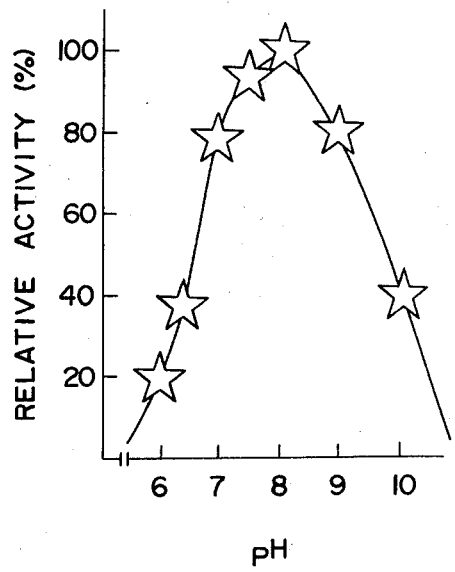
Figure 5:
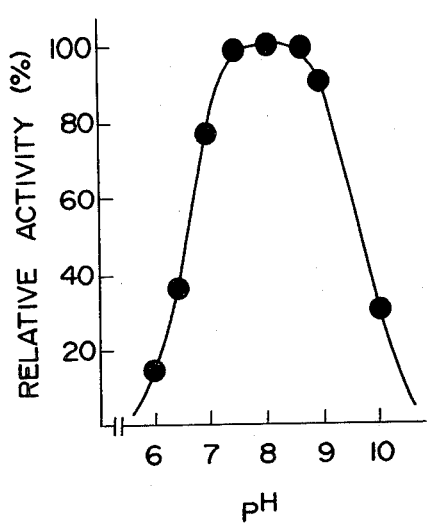
Figure 6:
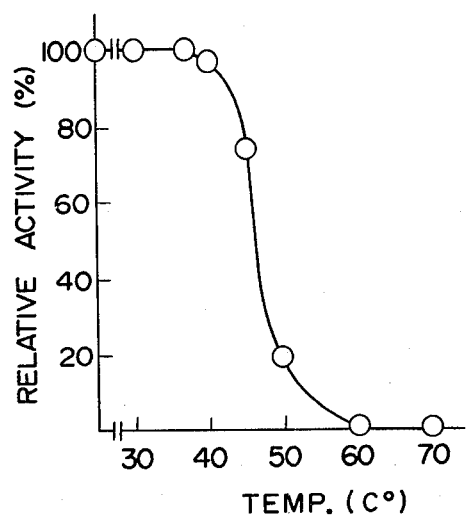
FIGS. 6–10 are heat stability curves of the amine oxidase produced by the five strains.
Figure 7:
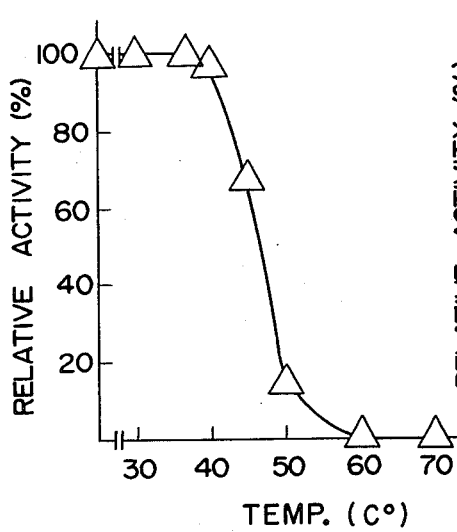
Figure 8:
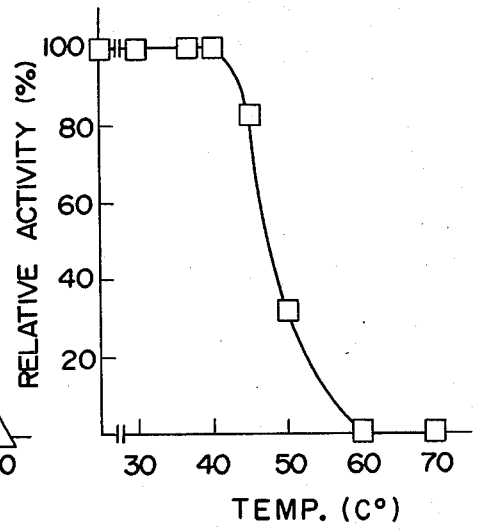
Figure 9:
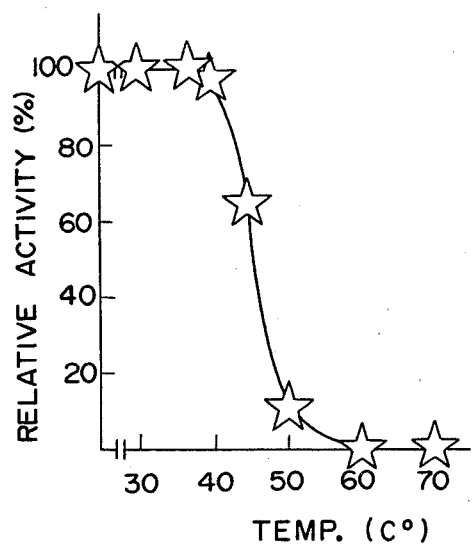
Figure 10:
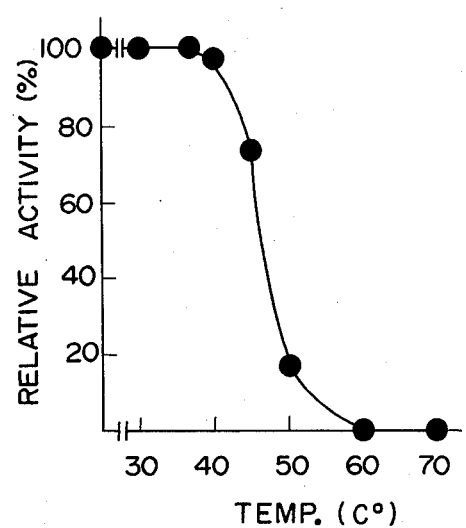
Figure 11:
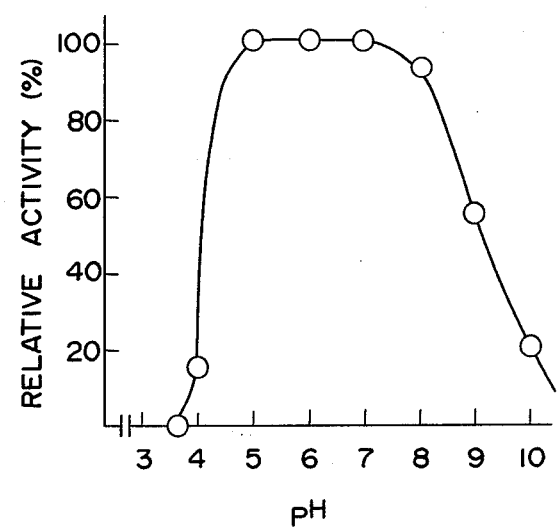
FIGS. 11–15 are pH stability curves of the amine oxidase produced by the five strains.
Figure 12:
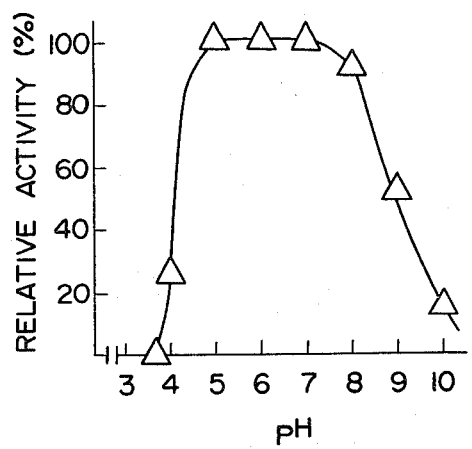
Figure 13:
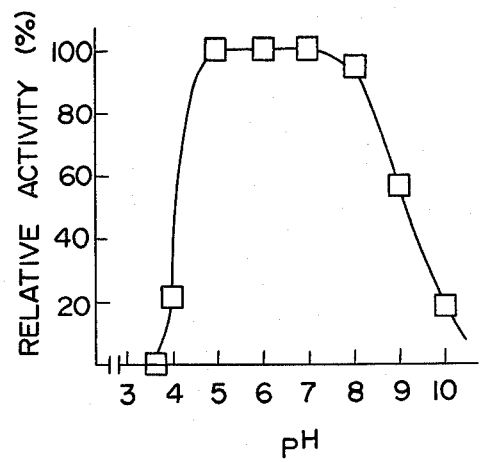
Figure 14:
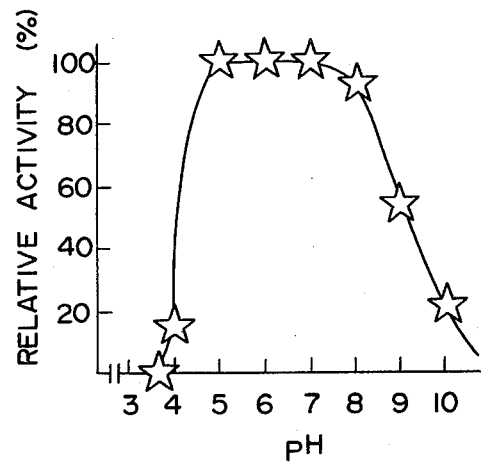
Figure 15:
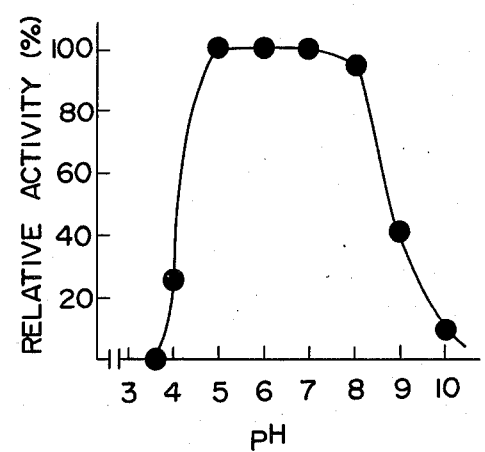

Amine oxidase activities at various pH's are shown in FIGS. 1–5. (FIG. 1: M 4805, FIG. 2: M 4690, FIG. 3: M 4648, FIG. 4: M 5051, FIG. 5: M 4175)
Optimum pH of the amine oxidase is as follows:
M 4805: pH 7.5–8.5 (FIG. 1)
M 4690: pH 7.5–8.5 (FIG. 2)
M 4648: pH 7.5–8.5 (FIG. 3)
M 5051: pH 7.5–8.5 (FIG. 4)
M 4175: pH 7.5–8.5 (FIG. 5)

(3) Heat stability

An enzyme solution (0.1 ml) mixed with a 0.1 M phosphate buffer (pH 7.0, 0.9 ml) is incubated at various temperatures of 0°, 30°, 37°, 40°, 50°, 60° and 70° C. for 10 minutes, and the remaining enzyme activity is measured according to an assay method. The results are shown in FIGS. 6–10. (FIG. 6: M 4805, FIG. 7: M 4690, FIG. 8: M 4648, FIG. 9: M 5051, FIG. 10: M 4175). Each enzyme is stable up to 40° C. and completely denatured over 60° C.

(4) pH stability

Each enzyme solution (0.1 ml) mixed with 0.1 M acetate buffer (pH 3–6, 0.9 ml), 0.1 M phosphate buffer (pH 6–8, 0.9 ml) or 0.1 M Tris-HCl buffer (pH 8–10, 0.9 ml), respectively, is incubated at 37° C. for three hours. 100 μl of the said incubated enzyme solutions are assayed according to an assay method for the enzyme. The results are shown in FIGS. 11–15. (FIG. 11: M 4805, FIG. 12: M 4690, FIG. 13: M 4648, FIG. 14: M 5051, FIG. 15: M 4175).
Each enzyme is stable at pH 5–7.

(5) Substrate specificities

Each enzyme solution (100 μl) is assayed with the following monoamines, amino acids and peptides according to an assay method. The relative activities are shown in the following table (n-butylamine is used as the standard):

| Substrate | Enzyme | | | | |
|---|---|---|---|---|---|
| | M 4805 | M 4690 | M 4648 | M 5051 | M 4175 |
| ethylamine | 47.6 | 49.4 | 38.0 | 50.0 | 42.2 |
| n-propylamine | 56.1 | 64.7 | 55.4 | 73.9 | 50.6 |
| n-butylamine | 100.0 | 100.0 | 100.0 | 100.0 | 100.0 |
| n-amylamine | 122.0 | 117.6 | 108.7 | 113.6 | 120.5 |
| n-hexylamine | 113.4 | 115.3 | 102.3 | 102.3 | 107.2 |
| benzylamine | 20.0 | 29.4 | 34.8 | 31.8 | 26.5 |

-continued

| Substrate | Enzyme | | | | |
|---|---|---|---|---|---|
| | M 4805 | M 4690 | M 4648 | M 5051 | M 4175 |
| tyramine | 80.5 | 82.4 | 55.4 | 80.7 | 86.7 |
| Gly—OMe | 9.4 | 9.6 | 6.5 | 9.4 | 10.1 |
| Gly—OEt | 11.3 | 11.5 | 7.8 | 11.3 | 12.1 |
| Gly—Gly—Gly—OMe | 9.4 | 9.6 | 6.5 | 9.4 | 10.1 |
| Gly—ONH$_2$ | 2.3 | 2.4 | 1.6 | 2.3 | 2.5 |
| Gly—OBzl | 2.2 | 2.2 | 1.5 | 2.2 | 2.3 |
| Gly—Gly—ONH$_2$ | 1.7 | 1.7 | 1.2 | 1.7 | 1.8 |
| Gly—Leu—ONH$_2$ | 0.3 | 0.3 | 0.2 | 0.3 | 0.4 |
| Gly—Gly—Gly—Ala—ONH$_2$ | 0.3 | 0.3 | 0.2 | 0.3 | 0.4 |
| Gly | 0.2 | 0.2 | 0.1 | 0.2 | 0.2 |
| Gly—Gly | 0.3 | 0.3 | 0.2 | 0.3 | 0.4 |

The enzyme of the present invention also has weak activity on diamines.

(6) Molecular weight

The molecular weight of the enzyme is measured by the gel filtration method using Sephadex G-100 (product of Pharmacia Co., trademark). The results are shown as follows:
M 4805: about 76,000–80,000
M 4690: about 76,000–80,000
M 4648: about 76,000–80,000
M 5051: about 76,000–80,000
M 4175: about 76,000–80,000

[Assay method for enzyme activity]

An assay method for amine oxidase of the present invention is as follows:

| | |
|---|---|
| 0.2 M Tris-HCl buffer (pH 8.0) | 0.1 ml |
| 0.2% phenol | 0.05 ml |
| 0.3% 4-aminoantipyrine | 0.05 ml |
| 0.05% peroxidase (Sigma Type I) | 0.05 ml |
| 0.1 M n-butylamine (pH 7.0) | 0.1 ml |
| distilled water | 0.05 ml |

The above reaction mixture (0.4 ml) in a test tube is pre-incubated at 37° C. for 3 minutes. The enzyme solution (100 μl) is added thereto and the mixture is incubated at 37° C. for 5 mins. The reaction is stopped by adding ethanol (2.5 ml) and the mixture is colorimetrically measured at 480 nm. One unit (U) is defined as 1 μmole of hydrogen peroxide liberated in one minute.

$$U/ml = 0.35 \times \frac{\Delta O.D._{480}}{\text{reaction time (min.)} \times \text{amount of enzyme (ml)}} \times \text{dilution ratio}$$

The enzyme amine oxidase having the above enzymatic properties has various utilities such as quantitative determination of amine, food production or medicaments. The enzyme can be used for convenient analysis of amine in specimens, for example the determination of amine in meat processing such as the determination of the freshness of meat by assaying tyramine; determination of amine liberated from decarboxylation of amino acids such as the assay of histamine formed from L-histidine by the action of L-histidine decarboxylase; and assaying the enzymatic activity of leucine aminopeptidase, for example by determining the enzymatic reaction product from a synthetic substrate, L-leucine-substituted methyamide, such as L-leucyl-n-butylamide and L-leucyl-tyramine, by the action of leucine aminopeptidase or aminopeptidase. These assays can be effected by measuring the consumed oxygen or liberated hydrogen peroxide in the reaction.

The following examples illustrate the present invention but are not to be construed as limiting.

EXAMPLE 1

A medium (500 ml, pH 6.0) comprising glucose 2%, potato extract 50 ml (extracted from potatoes 300 g by water 1 lit.), potassium mono phosphate 0.5%, magnesium sulfate 0.25% and n-butylamine 0.1% was separated into five 500 ml Erlenmeyer flasks each of 100 ml volume and sterilized at 120° C. for 20 minutes. The strains *Eurotium chevalieri* M 4805 FERM-P No. 5869, *Neosartorya fischeri* M 4690 FERM-P No. 5868, *Petromyces alliaceus* M 4648 FERM-P No. 5867, *Eupenicillium parvum* M 5051 FERM-P No. 5879 and *Talaromyces flavus* var. *flavus* M 4175 FERM-P No. 5866 were inoculated, respectively, and the mixtures were shake cultured at 30° C. for 24 hours at 300 rpm. The cultured liquid was filtered and the obtained cells were washed with distilled water and filtered. The thus-obtained cells were ruptured by adding twice the amount of sea sand (product of Nakarai Chem. Co.); then 0.1 M phosphate buffer (pH 7.0, about twice volume of cells) was added for extraction of the enzyme. The material was centrifuged so as to obtain a supernatant solution containing amine oxidase. The enzymatic activities of the supernatant solution are as follows:

| Strain | Enzymatic activity (U/ml cultured liquid) |
| --- | --- |
| M 4805 | 0.051 |
| M 4690 | 0.038 |
| M 4648 | 0.060 |
| M 5051 | 0.052 |
| M 4175 | 0.046 |

EXAMPLE 2

A medium (20 lit.) of the same composition as in Example 1 was inserted in 30 lit. jar-fermenter and sterilized. Seed culture (200 ml) of *Eurotium chevalieri* M 4805 FERM-P No. 5869, precultured in same was as in Example 1, was inoculated and the mixture was cultured at 30° C. for 20 hours. The cultured cells (about 150 g, wet wt.) were collected by filtration.

The thus-obtained cells were inoculated into a sterilized medium (20 lit., pH 6.0) comprising glucose 3%, potassium monophosphate 0.1%, magnesium sulfate 0.05%, potassium chloride 0.05% and n-butylamine 0.1% and cultured at 30° C. for 20 hours at 260 rpm. The cultured cells were collected by filtration, washed with water and filtered to obtain the cells (about 150 g, wet wt.). The thus-obtained cells were ruptured by adding twice the amount of sea sand (about 300 g), extracted with 0.1 M phosphate buffer (pH 7.0) and centrifuged to obtain a supernatant solution containing amine oxidase (about 310 ml, 0.5 U/ml).

The supernatant was concentrated about five-fold by a 30% solution of carbowax 20000 (product of Wako Pure Chem. Co.) dissolved in 0.1 M phosphate buffer (pH 7.0) and dialyzed against 0.1 M phosphate buffer solution (pH 7.0). The dialyzate (about 65 ml) was charged on a column (3×80 cm) of Sephadex G-100 and the fractions were collected containing amine oxidase to obtain a solution of amine oxidase (about 210 ml, 32 U). The solution was concentrated about ten-fold by 30% carbowax 20000 solution dissolved in 0.1 M phosphate buffer (pH 7.0), then dialyzed against 0.005 M phosphate buffer solution (pH 7.0) for 48 hours. The dialyzate (about 25 ml) was charged on a column (1.5×20 cm) of DEAE-cellulose (product of Seikagaku Kogyo Co.) previously buffered with a 0.005 M phosphate buffer solution (pH 7.0) to adsorb the amine oxidase. The amine oxidase was eluted by eluting with twice the volume of the column, of 0.005 M, 0.01 M and 0.025 M phosphate buffers (pH 7.0). The eluates were combined to obtain an amine oxidase solution (about 135 ml, 85U). This amine oxidase solution was concentrated about twelve-fold by 30% solution of carbowax 20000 dissolved in 0.1 M phosphate buffer (pH 7.0) and dialyzed to obtain the enzyme solution (9.5 ml, 8.2 U/ml, activity recovery 50.3%) which was lyophilized to obtain a powder of amine oxidase (18.5 mg).

What is claimed is:

1. A process for the production of amine oxidase, which comprises culturing an amine-oxidase-producing microorganism selected from the group consisting of *Talaromyces flavus* var. *flavus* M 4175 FERM-P No. 5866, *Eupenicillim parvum* M 5051 FERM-P No. 5870, *Petromyces alliaceus* M 4648 FERM-P No. 5867, *Neosaytorya fischeri* M 4690 FERM-P No. 5868 and *Eurotium chevalieri* M 4805 FERM-P No. 5869, and isolating the thus-prepared amine oxidase from the cultured medium.

* * * * *